United States Patent [19]

Maschmeyer et al.

[11] Patent Number: 5,578,546
[45] Date of Patent: Nov. 26, 1996

[54] CATALYST FOR PREPARING BIS-PARA-AMINOCYCLOHEXYLMETHANE CONTAINING A LOW PROPORTION OF TRANS/TRANS ISOMER BY HYDROGENATION OF METHYLENEDIANILINE

[75] Inventors: Dietrich Maschmeyer, Marl; Gerhard Thelen, Nottuln, both of Germany

[73] Assignee: Huels Aktiengesellschaft, Marl, Germany

[21] Appl. No.: 285,527

[22] Filed: Aug. 4, 1994

[30] Foreign Application Priority Data

Aug. 20, 1993 [DE] Germany .......................... 43 28 007.2

[51] Int. Cl.⁶ ..................................... B01J 23/46
[52] U.S. Cl. ......................... 502/327; 502/326; 502/332; 502/355
[58] Field of Search ................... 502/302, 326, 502/327, 332, 355

[56] References Cited

U.S. PATENT DOCUMENTS

| | | | |
|---|---|---|---|
| 2,511,028 | 6/1950 | Whitman | 260/563 |
| 2,606,925 | 8/1952 | Whitman | 260/563 |
| 2,606,928 | 8/1952 | Barkdoll et al. | 260/563 |
| 3,347,917 | 10/1967 | Arthur | 260/563 |
| 3,591,635 | 7/1971 | Farrissey, Jr. et al. | 260/563 B |
| 3,636,108 | 1/1972 | Brake | 260/563 D |
| 3,644,522 | 2/1972 | Brake et al. | 260/563 D |
| 3,697,449 | 10/1972 | Brake | 252/474 |
| 3,856,862 | 12/1974 | Chung et al. | 260/563 B |
| 4,051,072 | 9/1977 | Bedford et al. | 252/464 |
| 4,166,100 | 8/1979 | Vorobiev et al. | 423/626 |
| 4,380,510 | 4/1983 | D'Aniello, Jr. | 252/466 PT |
| 4,394,298 | 7/1983 | Nowack et al. | 252/438 |
| 4,448,995 | 5/1984 | Allen | 564/451 |
| 4,513,101 | 4/1985 | Peters et al. | 502/304 |
| 5,360,934 | 11/1994 | Vedage et al. | 564/451 |

FOREIGN PATENT DOCUMENTS

| | | |
|---|---|---|
| 0066212 | 12/1982 | European Pat. Off. . |
| 0121735 | 10/1984 | European Pat. Off. . |
| 0231788 | 8/1987 | European Pat. Off. . |
| 0324190 | 7/1989 | European Pat. Off. . |
| 0392435 | 10/1990 | European Pat. Off. . |
| 0630882 | 12/1994 | European Pat. Off. . |
| 2354815 | 1/1978 | France . |
| 2432479 | 2/1980 | France . |
| 2520848 | 12/1975 | Germany . |
| 2745172 | 4/1979 | Germany . |
| 4028270 | 3/1992 | Germany . |

*Primary Examiner*—Shrive Beck
*Assistant Examiner*—Timothy H. Meeks
*Attorney, Agent, or Firm*—Oblon, Spivak, McClelland, Maier & Neustadt, P.C.

[57] ABSTRACT

A catalyst for preparing bis-para-aminocyclohexylmethane by hydrogenation of methylenedianiline, comprising ruthenium or rhodium in an amount of from 0.05 to 8% by weight, applied in a layer thickness of from 5 to 150 μm to a support comprising a calcined and surface-rehydrated transition alumina, wherein a suspension of 10 g of the transition alumina in 300 ml of water at 25° C. has an equilibrium pH of at least 8.2 after 60 minutes and after addition of 10 ml of 0.1N hydrochloric acid to this suspension it has a pH of at least 6.0 after 30 minutes.

11 Claims, No Drawings

CATALYST FOR PREPARING BIS-PARA-AMINOCYCLOHEXYLMETHANE CONTAINING A LOW PROPORTION OF TRANS/TRANS ISOMER BY HYDROGENATION OF METHYLENEDIANILINE

BACKGROUND OF THE INVENTION

1. Field of the Invention

The invention relates to a ruthenium or rhodium catalyst for hydrogenating methylenedianiline (MDA) to bis-para-aminocyclohexylmethane (PACM), in which the catalytically active metal is applied to a support made of a special transition alumina.

2. Discussion of the Background

The hydrogenation of methylenedianiline was developed around 1947 and applied on an industrial scale around 1965. Most disclosures describe processes which are carried out in suspension with the addition of a substantially unreactive solvent. The hydrogenation product PACM has been gradually used in more and more applications in which the isomer ratios are very important.

U.S. Pat. No. 2,511,028 and U.S. Pat. No. 2,606,925 describe, in general terms, the preparation of PACM by hydrogenation of MDA over a ruthenium catalyst. U.S. Pat. No. 2,606,928 shows the preparation of PACM having an increased cis-content; the catalyst is ruthenium with addition of alkali on activated carbon. A further development is described in U.S. Pat. No. 3,697,449, the alkali-moderated catalyst being used on supports of aluminum oxide, barium sulfate or kieselguhr in pulverulent form; according to U.S. Pat. No. 3,636,108 the alkali-moderated catalyst is additionally admixed with alkali metal amide or methoxide.

U.S. Pat. No. 3,636,108 and U.S. Pat. No. 3,644,522 describe how the trans/trans isomer content can be shifted during the hydrogenation or subsequently. The catalyst used is ruthenium, if desired modified with alkali, on a weakly alkaline or amphoteric support such as potassium carbonate or alkaline earth metal oxide. Further properties of ruthenium catalysts, of which mention may be made, are disclosed in U.S. Pat. No. 4,448,995 and U.S. Pat. No. 4,394,298 and also DE-A 40 28 270, DE-A 27 45 172 and DE-A 25 20 848.

According to U.S. Pat. No. 3,591,635, U.S. Pat. No. 3,856,862 and EP-A 0 662 212 and EP-A 0 392 435, rhodium catalysts are used for the hydrogenation.

Finally, European Patent 0 324 190 describes a process for hydrogenating MDA in a fixed bed; the addition of solvent is merely optional. Use of a ruthenium catalyst (0.1–5% of ruthenium) on alumina with a relatively deeply impregnated shell (at least 50 μm), a BET surface area of from 70 to 280 $m^2/g$ and an average pore diameter of from 1.0 to 32.0 nm makes it possible to achieve high activity and a low proportion of trans/trans isomers. The process is preferably carried out in a solvent-free melt.

From the abovementioned literature citations, it is evident that the hydrogenation of substituted anilines, in particular MDA, to products having a high proportion of cis or cis/cis isomer, presents a significant problem, particularly with regard to finding a catalyst which promotes this selectivity. This applies particularly to carrying out the reaction in a fixed bed and could be the reason for the low success rate in this area.

Furthermore, it is apparent that there is a preconception that the isomer distribution of the product can only be affected by altering the reaction conditions, which must be particularly accurately adhered to, by doping the support with alkali metal or alkaline earth metal compounds or by the addition of ammonia during the reaction. The measures of alkalization and addition of ammonia are also said to effect a suppression of the deamination and the isomerization of amino groups. However, lowering the reaction temperature has technical limits because of diminished catalyst activity. In addition, such a doping with alkalis obviously makes it necessary, because of their good solubility, to apply the metallic active components of the catalyst in a relatively thick layer. However, the inward and outward transport of the reactants by diffusion is thereby made much more difficult, which, despite the relatively slow reaction, leads to the reaction rate and selectivity being controlled by the rate of material transport and not by the intrinsic performance of the active component. In addition, the channels of such deeply impregnated catalysts are all the more easily blocked by highly viscous materials such as high boilers, oligomers, carbon deposits, and the like as the average pore radius and pore volume become smaller. Additionally, a large BET surface area and a large average pore radius are required for optimal distribution and dispersion of the metal particles.

The process according to European Patent 0 324 190 already shows good activity values and a relatively small proportion of trans/trans isomer. However, the mechanical stability of the alumina supports used therein requires a high pretreatment temperature, through which the surface of these materials is relatively quickly deactivated.

Furthermore, studies of reaction kinetics have shown that the isomer distribution is not only a result of the acidity of the catalyst, but also of the residence time, and an increase in the latter shifts the distribution towards higher trans/trans contents, i.e. in the undesired direction, because the catalyst isomerizes more strongly. With increasing covering of the inner pores of a thick-shell-impregnated catalyst support, the diffusion coefficients of starting materials such as MDA and products such as PACM fall relatively quickly, so that after a relatively short catalyst operating time, not only does deactivation occur, but also the residence time increases in the catalyst interior and with it a shifting of the selectivity into unfavorable ranges. Since these factors cannot be compensated by an increase in temperature, because this would shift the selectivity further into the undesired range, the catalyst for such processes generally has to be replaced after a relatively short time. A need therefore continues to exist for a more effective catalyst for the hydrogenation of methylenedianiline.

SUMMARY OF THE INVENTION

Accordingly, one object of the invention is to provide a more effective ruthenium or rhodium catalyst, based on an improved support, which, in the hydrogenation of MDA to PACM, results in longer catalyst lifetime and leads to products having a low trans/trans content.

Briefly, these objects and other objects of the present invention as hereinafter will become more readily apparent can be attained in a catalyst for the hydrogenation of methylenedianiline to bis-p-aminocyclohexylmethane which comprises ruthenium or rhodium in an amount of from 0.05 to 8 % by weight applied in a layer thickness of from 5 to 150 μm to a support comprising a calcined and surface-rehydrated transition alumina, wherein a suspension of 10 g of said transition alumina in 300 ml of water at 25° C. has an equilibrium pH of at least 8.2 after 60 minutes and after addition of 10 ml of 0.1N hydrochloric acid to this suspension it has a pH of at least 6.0 after 30 minutes.

DETAILED DESCRIPTION OF THE PREFERRED EMBODIMENTS

It has now been found that certain aluminas are very good buffer substances for acidity, if care is taken to ensure that the surface of the catalyst support is still sufficiently chemically active and has not been deactivated by thermal treatment. This is the case if the support is present in the form of the compounds boehmite, hydrargillite or bayerite, preferably hydrargillite. The support then exhibits characteristics which reflect its treatment with alkali, but with the difference that alumina is insoluble under the reaction conditions, while alkali components are mobile in the corresponding reaction media and, in some cases, may be concentrated or depleted in certain zones, which can result in localized shifting of the isomer distribution formed into unfavorable ranges. However, alumina is very sparingly soluble in the normal pH range between 4 and 10, so that basic buffer groups remain fixed in position on the surface of catalyst supports.

The invention therefore provides catalysts which promote the hydrogenation of methylenedianiline to form bis-para-aminocyclohexylmethane. The present catalyst contains ruthenium or rhodium in an amount of from 0.05 to 8% by weight, preferably from 0.2 to 3% by weight, which is applied with a layer thickness of from 5 to 150 µm, preferably from 10 to 80 µm, onto a support comprising a calcined and surface-rehydrated transition alumina, where a suspension of 10 g of this alumina in 300 ml of water at 25° C. has an equilibrium pH of at least 8.2 after 60 minutes. After addition of 10 ml of 0.1N hydrochloric acid to this suspension, it still has a pH of at least 6.0 after 30 minutes.

The required reactivity and buffering ability of the catalyst support to be used are determined in the invention by measurement of the buffering against hydrochloric acid in an aqueous suspension. Practical experiments have shown that ground, calcined and surface-rehydrated transition aluminas should, in a suspension of 10 g in 300 ml of water at 25° C., give an equilibrium pH of at least 8.2. The total buffering capacity is determined by adding successive amounts of hydrochloric acid to such a suspension. Sufficient capacity and activity are indicated, if, after addition of 10 ml of 0.1N hydrochloric acid to this suspension at 25° C., the pH is still at least 6.0 after 60 minutes.

It has additionally been found that catalyst supports having a very rough surface permit rapid exchange of material. This roughness can best be described by the peak-to-valley height. This should lie between 50 and 200 µm.

The catalysts of the invention avoid many disadvantages of the systems used in the past. In particular, if a positionally fixed buffering capacity is present with a very high density per unit area, as is particularly the case on boehmitic and hydrargillitic surfaces, the layer thickness of the active components can be very much reduced. In some circumstances this can shorten the diffusion paths so much that covering of the internal porosity of the support by high boiling materials, and the like over a long time may no longer have any significant affect on the reaction. The accessibility of the inner surface can also be substantially further improved by making the roughness of the support surface very high.

The catalysts of the invention have a BET surface area of at least 70 m$^2$/g and an open porosity of at least 0.1 ml/g.

The invention also provides a process for preparing the catalysts of the invention, in which the catalyst support is sprayed with a dilute ruthenium nitrosyl nitrate solution while being circulated at a temperature of at least 80° C. and is then dried. The reduction is subsequently carried out in a stream of hydrogen at a pressure of at least 0.3 bar at temperatures between 70° and 400° C., preferably from 140° to 250° C.

Suitable support embodiments may be formed from materials such as oxides and hydroxides of iron, yttrium or of lanthanide elements, which exhibit similar action to alumina.

Aluminas which at first do not show the desired buffering action can be correspondingly modified by precipitation or by coating the surface with oxides and hydroxides of aluminum, iron, yttrium or the lanthanides via the sol/gel process. This should give an open porosity of at least 0.04 ml/g and a peak-to-valley height of at least 50 µm.

Having now generally described this invention, a further understanding can be obtained by reference to certain specific examples which are provided herein for purposes of illustration only and are not intended to be limiting unless otherwise specified.

EXAMPLE 1

(Comparative)

Characterization of the support

A 10 g amount of alumina support SPHERALIT® SP 521 C from Procatalyse are ground and suspended in 300 ml of water at 25° C. To exclude the buffering action of carbon dioxide, nitrogen is passed through the suspension. After 60 minutes, an equilibrium pH of 6.7 is obtained. A 10 ml amount of 0.1N hydrochloric acid is then added. After 60 minutes, the pH of the suspension is 4.3.

The support is in the form of extrudites having a diameter of 1.6 mm. The surface is very smooth and has a peak-to-valley height of less than 20 µm.

Preparation and testing of a catalyst with the prepared support:

The support material is heated to a temperature from 90° to 100° C. in a rotating drum and is sprayed with a 1% strength solution of ruthenium nitrosyl nitrate in water through a fine nozzle, until 1% of ruthenium has been applied to the support. The material is dried at 200° C. The catalyst thus prepared is installed in a tube reactor 1 m in length and is reduced at 200° C. under flowing hydrogen at a pressure of 1 bar. Subsequently, a melt of MDA is pumped under 300 bar hydrogen pressure at 150° C. to trickle through the reactor at a weight hourly space velocity of 0.1 g of MDA/(g of catalyst . h).

After 3 days of operation, the MDA conversion is 41% with a residual MDA content of 59% and 17% of semi-hydrogenated product; the proportion of trans/trans isomer in the fully hydrogenated product is 22%.

In order to improve the conversion, the temperature is increased to 180° C. This raises the MDA conversion to 85%, the content of semi-hydrogenated material in the product is 20%, and the trans/trans content in the fully hydrogenated product is 28.5%.

EXAMPLE 2

(Invention)

Characterization of the support:

A 10 g a amount of ALCOA® F-1 alumina is ground and suspended in 300 ml of water at 25° C. To avoid buffering by carbon dioxide, nitrogen is again passed through the suspension. An equilibrium pH of 9.2 is obtained after 60 minutes. A 10 ml amount of 0.1N hydrochloric acid is then added. After 60 minutes the pH of the suspension is 7.3.

The support is in the form of irregular fragments with a size of from 1 to 3 mm. The surface is very rough and has a peak-to-valley height of about 150 μm.

Preparation and testing of a catalyst with the prepared support:

The support material is heated to a temperature from 90 to 100° C. in a rotating drum and is sprayed with a 1% strength solution of ruthenium nitrosyl nitrate in water through a fine nozzle, until 1% of ruthenium has been applied to the support. The material is dried at 200° C. The catalyst thus prepared is installed in a tube reactor 1 m in length and is reduced at 200° C. under flowing hydrogen at a pressure of 1 bar. Subsequently, a melt of MDA is pumped under 300 bar hydrogen pressure at 150° C. to trickle through the reactor at a weight hourly space velocity of 0.1 g of MDA/(g of catalyst . h).

After 3 days of operation the MDA conversion is over 99% with a residual MDA content of 0.28% and 4.9% of semi-hydrogenated product; the proportion of trans/trans isomer in the fully hydrogenated product is 23.3%. In order to modify the conversion, the temperature is lowered to 140° C. This reduced the MDA conversion to 97%. The content of semi-hydrogenated material in the product is 18%, and the trans/trans content in the fully hydrogenated product is 20.5%.

It is thus demonstrated that at a substantially higher conversion of MDA, the content of trans, and particularly of trans/trans isomer, can be maintained at the desired level, i.e. that the isomerization activity of the catalyst is considerably lower.

EXAMPLE 3

Long-Term Behavior (Comparative)

The catalyst of Comparative Example 1 was installed in a tube reactor 1 m in length and was reduced at 200° C. under flowing hydrogen at a pressure of 1 bar. Subsequently, a melt of MDA was trickled through the reactor under 300 bar hydrogen pressure, initially at 150° C., later at different temperatures, at a weight hourly space velocity of 0.1 g of MDA/(g of catalyst . h). The contents of MDA, semi-hydrogenated product and proportion of trans/trans isomer in the PACM developed in the product over the running time are shown in Table 1.

TABLE 1

| Running time d | Temperature °C. | MDA % | semi-hydrogenated product % | trans/trans in the PACM % |
| --- | --- | --- | --- | --- |
| 3 | 150 | 58.6 | 17.2 | 22.6 |
| 5 | 150 | 64.7 | 12.5 | 22.7 |
| 9 | 150 | 54.8 | 16.9 | 20.6 |
| 10 | 160 | 49.9 | 16.9 | 19.9 |
| 11 | 180 | 15.0 | 56.9 | 28.3 |
| 12 | 180 | 15.2 | 21.1 | 26.7 |
| 13 | 180 | 17.3 | 29.7 | 27.1 |
| 14 | 180 | 19.1 | 33.6 | 25.9 |

The experiment shows that at 150° C. only very low conversions are achieved. Increasing the temperature increases the conversions, although still not into a satisfactory range, but at the same time the content of trans/trans isomer in the product already rises from 20 to 25.5%. With a longer residence time at 180° C., it can be seen that the conversion decreases greatly due to ageing of the catalyst. The catalyst of Comparative Example 1 is therefore not very suitable for industrial use.

EXAMPLE 4

Long-Term Behavior to the (Invention)

The catalyst of Example 2 was installed in a tube reactor 1 m in length and was reduced at 200° C. under flowing hydrogen at a pressure of 1 bar. Subsequently, a melt of MDA was trickled through the reactor under 300 bar hydrogen pressure, initially at 150° C., later at different temperatures, at a weight hourly space velocity of 0.1 g of MDA/(g of catalyst . h). The contents of MDA, semihydrogenated product and proportion of trans/trans isomer in the PACM developed in the product over various running times are shown in Table 2.

TABLE 2

| Running time d | Temperature °C. | MDA % | semi-hydrogenated product % | trans/trans in the PACM % |
| --- | --- | --- | --- | --- |
| 3 | 150 | 0.28 | 4.90 | 23.3 |
| 5 | 150 | 0.09 | 1.08 | 25.4 |
| 9 | 150 | 0.30 | 2.10 | 25.2 |
| 15 | 150 | 0.22 | 1.86 | 25.3 |
| 17 | 140 | 1.89 | 14.00 | 20.6 |
| 21 | 140 | 4.00 | 21.10 | 20.0 |
| 24 | 150 | 0.74 | 6.60 | 24.6 |
| 26 | 150 | 1.00 | 8.00 | 24.2 |

The experiment shows that at 150° C. over a long time, very high conversions can be achieved with a relatively low content of trans/trans isomer. Reducing the temperature allows the content of trans/trans isomer to be controlled with conversions falling only slightly. After a running time of 26 days and a much greater throughput of starting material than in Comparative Example 3, excellent conversions are still obtained, as are nowhere near achieved in Comparative Example 3. This clearly shows the superiority, based on the special properties of the support and the preparative process, of the catalyst of the invention.

EXAMPLE 5

Rhodium Catalyst According to the Invention

In the same way as described in Example 2, ALCOA® F-1 alumina is sprayed, at from 90° to 100° C. in the rotating drum, with a 1% strength rhodium nitrate solution in water through a fine nozzle, until 1% of rhodium has been applied to the support. The material is dried at 200° C. The catalyst thus prepared is installed in a tube reactor 1 m in length and is reduced at 200° C. under flowing hydrogen at a pressure of i bar. Subsequently, a melt of MDA is pumped under 300 bar hydrogen pressure at 150° C. to trickle through the reactor at a weight hourly space velocity of 0.1 g of MDA/(g of catalyst . h).

After 3 days of operation, an MDA conversion of about 98.8 with a residual MDA content of 1.2% and 6.1% of semi-hydrogenated product are obtained. The proportion of trans/trans isomer in the fully hydrogenated product (PACM) is 24.4%. After a further 6 days of operation, the conversion is still 97.8% with an unchanged content of trans/trans isomer in the product.

These results show that the same method can be used to prepare rhodium catalysts which have similar properties to those of the ruthenium catalysts described earlier.

Having now fully described the invention, it will be apparent to one or ordinary skill in the art that many changes and modifications can be made thereto without departing from the spirit or scope of the invention as set forth herein.

What is claimed as new and is desired to be secured by Letters Patent of the United States is:

1. A catalyst for preparing bis-para-aminocyclohexylmethane by hydrogenation of methylenedianiline, comprising: ruthenium or rhodium in an amount of from 0.05 to 8% by weight, applied in a layer thickness of from 5 to 150 μm to a support comprising a calcined and surface-rehydrated transition alumina, wherein a suspension of 10 g of said transition alumina in 300 ml of water at 25° C. has an equilibrium pH of at least 8.2 after 60 minutes and after addition of 10 ml of 0.1N hydrochloric acid to this suspension it has a pH of at least 6.0 after 30 minutes.

2. The catalyst according to claim 1, wherein the amount of ruthenium or rhodium ranges from 0.2 to 3% by wt.

3. The catalyst according to claim 1, wherein the layer thickness of said ruthenium or rhodium ranges from 10 to 80 μm.

4. The catalyst according to claim 1 wherein the support has an internal BET surface area of at least 70 $m^2/g$ and an open porosity of at least 0.1 ml/g.

5. The catalyst according to claim 1 or 4, wherein the rehydrated alumina phase comprises predominantly hydrargillite or bayerite.

6. The catalyst according to claim 1 or 4 wherein the support has a very rough surface with peak-to-valley heights of between 50 and 200 μm.

7. A catalyst for preparing bis-paraaminocyclohexylmethane by hydrogenation of methylenedianiline, comprising:

ruthenium or rhodium in an amount of from 0.05 to 8% by weight, applied in a layer thickness of from 5 to 150 μm to a support comprising a calcined and surface-rehydrated transition alumina, which does not exhibit a buffering action to an acid treatment in which a suspension of 10 g of said alumina in 300 ml of water at 25° C. has an equilibrium pH of at least 8.2 after 60 minutes and, after the addition of 10 ml of 0.1 N HCl to the suspension, said alumina has a pH of at least 6.0 after 30 minutes, which alumina support is coated, via a sol/gel process, with a coating of an oxide or hydroxide of aluminum, iron, yttrium or a lanthanide metal, with the consequence that the coated alumina exhibits a buffering action which is an equilibrium pH of at least 8.2 after suspending a 10 g amount of the coated alumina in 300 ml of water at 25° C. for 60 minutes, and then, after addition of 10 ml of 0.1N HCl to the suspension, the aqueous suspension having an equilibrium pH of at least 6.0 after 30 minutes.

8. The catalyst according to claim 1 wherein the support has a BET surface area of at least 3 $m^2/g$, an open porosity of at least 0.04 ml/g and a peak-to-valley height of the surface of at least 50 μm.

9. A process for preparing a catalyst which comprises ruthenium or rhodium in an amount of from 0.05 to 8% by weight, applied in a layer thickness of from 5 to 150 μm to a support comprising a calcined and surface-rehydrated transition alumina, wherein a suspension of 10 g of said transition alumina in 300 ml of water at 25° C. has an equilibrium pH of at least 8.2 after 60 minutes and after addition of 10 ml of 0.1N hydrochloric acid to this suspension, the suspension has a pH of at least 6.0 after 30 minutes, comprising:

spraying a dilute ruthenium nitrosyl nitrate solution onto the support, while circulating the support at a temperature of at least 80° C.; and subsequently drying the sprayed support.

10. The process according to claim 9, wherein subsequent to drying the catalyst a further reduction is carried out in hydrogen at a pressure of at least 0.3 bar at temperatures between 70 and 400° C.

11. The process according to claim 10, wherein said further reduction is carried out at a temperature between 140° and 250° C.

* * * * *